United States Patent
Ploetz

[11] Patent Number: 5,896,437
[45] Date of Patent: Apr. 20, 1999

[54] X-RAY DIAGNOSTICS APPARATUS FOR TOMOSYNTHESIS HAVING A REFERENCE OBJECT IN FIXED RELATIONSHIP TO A RADIATION EMITTER

[75] Inventor: Josef Ploetz, Bensheim, Germany

[73] Assignee: Sirona Dental Systems GmbH & Co. KG, Bensheim, Germany

[21] Appl. No.: 08/858,602

[22] Filed: May 19, 1997

[30] Foreign Application Priority Data

May 17, 1996 [DE] Germany ................... 19619913

[51] Int. Cl.[6] .................................... G01N 23/00
[52] U.S. Cl. ............................... 378/2; 378/162
[58] Field of Search .......................... 378/2, 162

[56] References Cited

U.S. PATENT DOCUMENTS 5,070,454  12/1991  Griffith .
5,299,254  3/1994   Dancer et al. ................. 378/162
5,359,637  10/1994  Webber .
5,598,454  1/1997   Franetzki et al. .

FOREIGN PATENT DOCUMENTS 0 479 618  8/1992  European Pat. Off. .

Primary Examiner—Craig E. Church
Attorney, Agent, or Firm—Hill & Simpson

[57] ABSTRACT

An X-ray diagnostics apparatus for tomosynthesis has a radiation emitter and a reference object exclusively connected thereto so that the reference object has a fixed reference relationship to the radiation emitter. It is thus possible to determine the spacing of the radiation emitter from the radiation receiver and from the examination subject, the radiation angle and the transirradiation direction on the basis of the signals obtained from the radiation receiver upon transirradiation of the reference subject without having the reference object representing an impediment in the region of the examination subject.

10 Claims, 2 Drawing Sheets

ID="1"/>
X-RAY DIAGNOSTICS APPARATUS FOR TOMOSYNTHESIS HAVING A REFERENCE OBJECT IN FIXED RELATIONSHIP TO A RADIATION EMITTER

BACKGROUND OF THE INVENTION

1. Field of the Invention

The present invention is directed to an X-ray diagnostic apparatus for a tomosynthesis, and in particular to an apparatus of the type employing a reference object in the radiation beam proceeding from the radiation emitter.

2. Description of the Prior Art

PCT application WO 93/22 893 discloses a method with which it is possible to reconstruct an exposure of an examination subject without the projection angle α and the geometrical arrangement of the radiation emitter and radiation receiver and the focal plane being known. According to this method, a reference object of radiation-absorbing material having a known size and a known spacing from the radiation receiver is provided in the region of the radiation receiver, this reference object being projected onto the radiation receiver in every individual projection. The geometrical arrangement and the two-dimensional projection angle α for each individual projection can be determined on the basis of the two-dimensional spatial imaging of the reference on the radiation receiver.

A holder for positioning a radiation emitter of an X-ray diagnostic apparatus for tomosynthesis is disclosed in German OS 44 14 689, corresponding to U.S. Pat. No. 5,598,454. A bracket is coupled to the holder, at which—as viewed in the radiation propagation direction—a spherical reference object is arranged in front of the examination subject and a radiation receiver is arranged behind the examination subject. The spacing of the radiation from the reference object and from the radiation receiver, as well as the angle α of a ray beam emitted by the radiation emitter relative to a reference axis of the holder mechanism, are prescribed by the holder. It is also known to arrange the radiation source so as to be adjustable in a housing to which a positioning means for the reference object and the radiation receiver can be coupled.

In such known tomosynthesis systems, because the reference object is disposed in front of the examination subject and is mounted on a bracket connected to the holder for the radiation receiver, the reference object can constitute a nuisance or an impediment in setting up the apparatus and conducting the examination.

SUMMARY OF THE INVENTION

It is an object of the present invention to provide an X-ray diagnostic apparatus for tomosynthesis, which employs a reference object disposed in the radiation beam, but wherein the reference object is mounted in a manner which does not constitute a nuisance or an impediment to setting up or conducting the examination.

The above object is achieved in accordance with the principles of the present invention in an X-ray diagnostic apparatus for tomosynthesis having a radiation emitter and a radiation receiver and a reference object disposed therebetween, wherein the reference object is exclusively connected to the radiation emitter and has a fixed reference relationship to the radiation emitter.

It is especially advantageous for the reference object to be composed of a number of sub-objects that are fashioned beam-like and cross one another. The spacing of the radiation emitter from the radiation receiver, the incident angle (projection angle) and the irradiation direction can be determined by the projection of the reference object onto the radiation receiver and evaluation of the signals that are generated by the reference object. It is thus possible to obtain data for the calculation of a tomosynthesis exposure from the image signals that are acquired upon irradiation of the examination subject from different directions and derived from the radiation receiver.

Alternatively, the reference object can be formed of at least three sub-objects whose arrangement relative to one another deviates from a straight line. It is especially advantageous when the sub-objects or regions of the sub-objects differ in terms of their radiation absorption, so that the spacing, the irradiation angle and the irradiation direction can be determined in an unambiguous way.

DESCRIPTION OF THE PREFERRED EMBODIMENTS

Figure 1:
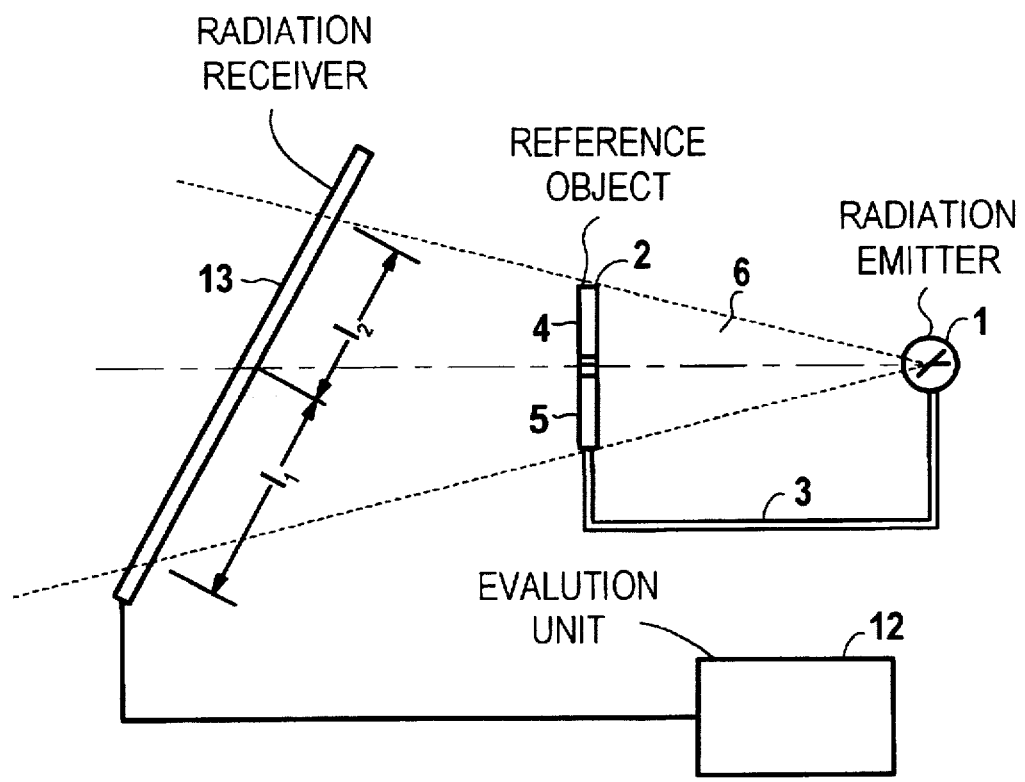
FIG. 1 is a schematic illustration of an X-ray diagnostics apparatus for tomosynthesis, with a reference object at a fixed position relative to the radiation source constructed in accordance with the principles of the present invention.
Figure 2:
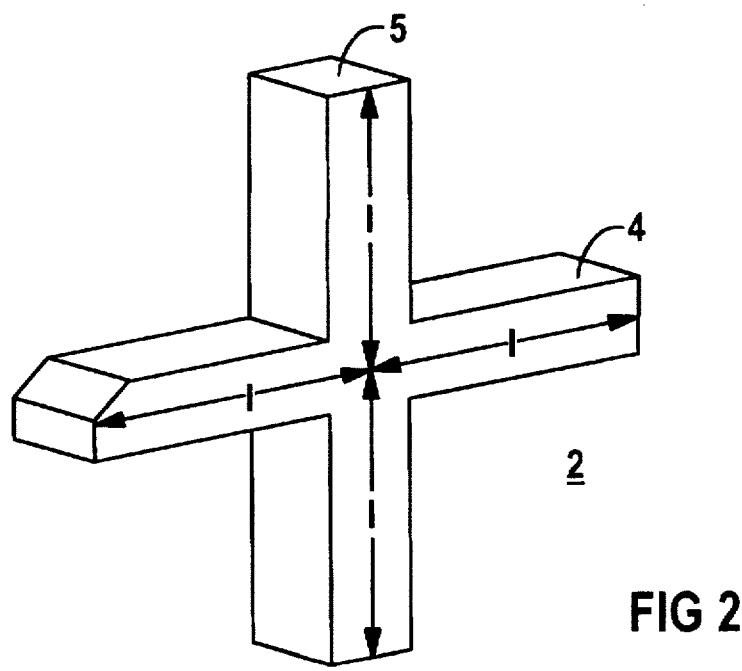
FIG. 2 shows a first exemplary embodiment of a reference object for the X-ray diagnostics apparatus according to FIG. 1.

The diagnostic apparatus shown in FIG. 1 has a radiation emitter 1, particularly a radiation source, to which a reference object 2 is exclusively connected so that the reference object 2 has a fixed reference relationship to the radiation emitter 1. To this end, the reference object 2 can, for example, be coupled exclusively to the radiation emitter 1 via a holder 3. The reference object 2 is preferably composed of at least two sub-objects 4 and 5, and is arranged such that it lies in the ray beam 6 that emanates from the radiation emitter 1. In the exemplary embodiment, the sub-objects 4 and 5 are fashioned beam-like and cross, as shown in FIG. 2. The length 1 of the beam sections of the sub-objects 4 and 5 can be the same or different. Preferably, however, the sub-objects 4 and 5 are differently fashioned in terms of their radiation absorption, so that the irradiation direction can also be defined in an unambiguous way, whereas the spacing from the radiation receiver 13 and the irradiation angle (in terms of magnitude) can already be determined when the lengths or dimensions of the sub-regions of the sub-objects 4 and 5 are known. The different radiation absorption characteristics can be effected by sub-regions of the sub-objects 4 and 5 differing in length and/or shape, or in some other way. It is also possible to make only one sub-region of one sub-object 4 and 5 different from its other sub-regions in terms of radiation absorption.

Figure 3:
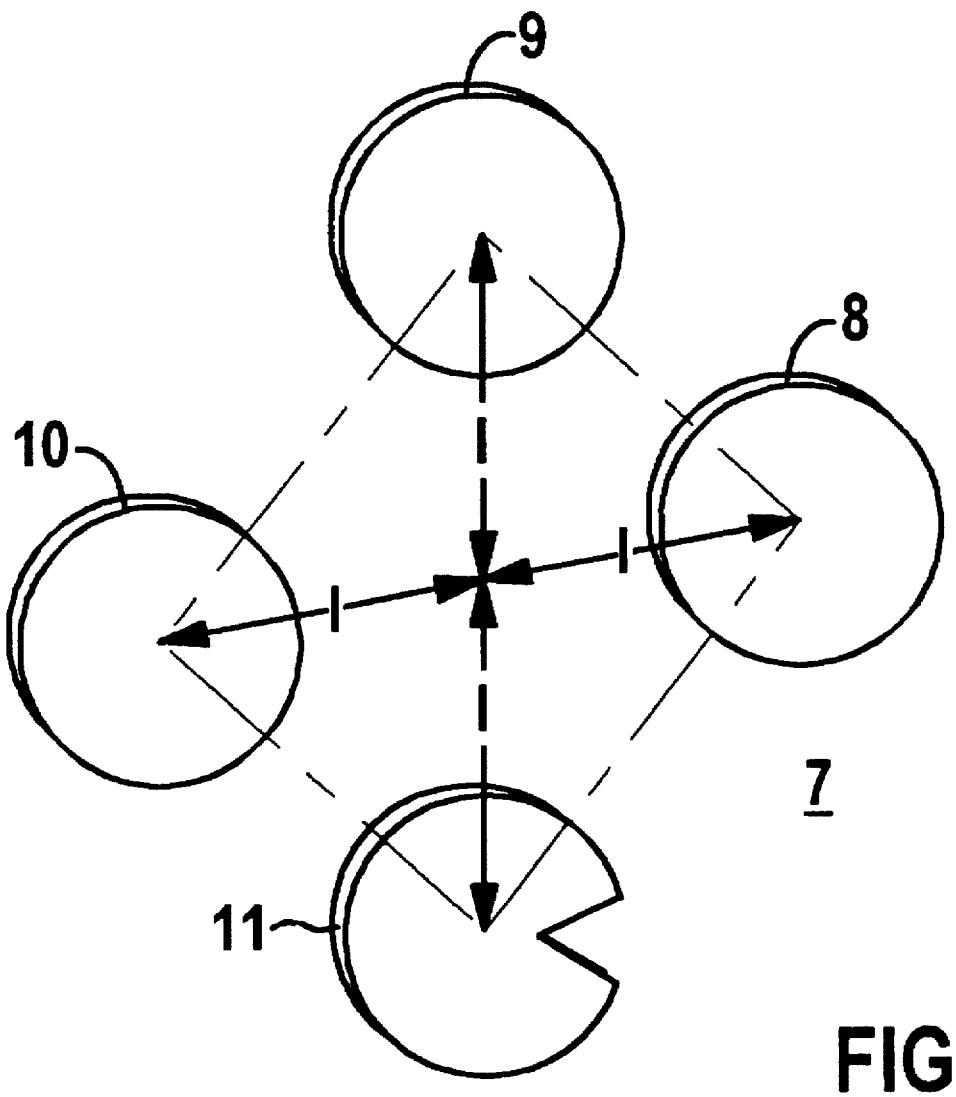
FIG. 3 shows second exemplary embodiment of a reference object for the X-ray diagnostics apparatus according to FIG. 1.

An alternative reference object 7 is shown in FIG. 3 having at least three sub-objects 8, 9 and 10. In the exemplary embodiment, a further sub-object 11 is provided. The arrangement of the sub-objects relative to one another deviates from a straight line. The sub-objects 8, 9, 10 and 11 form a geometrical body, for example a polygon, whereby the spacings of the sub-objects 8, 9, 10 and 11 are prescribed. In this exemplary embodiment, the sub-objects 8, 9, 10 and 11 are fashioned as disks; however, they can alternatively be spherical or assume some other shape. For unambiguous determination of the irradiation direction, at least one sub-object 11 can differ from the other sub-objects 8, 9 and 10 with respect to shape and/or radiation absorption.

All described reference objects and/or sub-objects can also be implemented in inverted form, i.e. as recesses in solid material. Disk-shaped solid material is preferably selected with outside dimensions that are not significantly larger than the reference object itself, and the recesses should proceed entirely or nearly entirely through the disk.

The signals of the radiation receiver 13 are supplied to an evaluation unit 12, so that the spacing, the irradiation angle and the irradiation direction can be determined from the signals obtained due to the projection of the reference object 2 onto the radiation receiver 13. When an examination subject—as seen from the direction of the radiation emitter 1—is located in front of the radiation receiver 13 and is transirradiated from different directions, then a tomosynthesis exposure of the examination subject can be produced on the basis of the signals of the examination subject received from each transirradiation direction as well as on the basis of the signals of the reference object.

Although the present invention has been described with reference to a specific embodiment, those of skill in the art will recognize that changes may be made thereto without departing from the scope and spirit of the invention as set forth in the appended claims.

I claim as my invention:

1. An X-ray diagnostic apparatus for tomosynthesis comprising:

a radiation emitter which emits an X-ray beam;

a reference object disposed in said X-ray beam;

a radiation receiver which is struck by said X-ray beam, attenuated by said reference object and an examination subject, and which emits electrical signals corresponding to X-rays incident thereon;

means for mounting said reference object in said X-ray beam by exclusively connecting said reference object to said radiation emitter for giving said reference object a fixed reference relationship to said radiation emitter; and means for generating a tomosynthesis image of said examination subject from said electrical signals.

2. An X-ray diagnostic apparatus as claimed in claim 1 wherein said reference object comprises at least two sub-objects.

3. An X-ray diagnostic apparatus as claimed in claim 2 wherein each of said sub-objects is formed as a beam, and wherein said sub-objects cross each other.

4. An X-ray diagnostic apparatus as claimed in claim 2 wherein said reference object comprises at least three sub-objects disposed in an arrangement relative to each other deviating from a straight line.

5. An X-ray diagnostic apparatus as claimed in claim 4 wherein said sub-objects form a geometrical body.

6. An X-ray diagnostic apparatus as claimed in claim 5 wherein said sub-objects form a polygon.

7. An X-ray diagnostic apparatus as claimed in claim 4 wherein said at least three sub-objects each comprise a sphere.

8. An X-ray diagnostic apparatus as claimed in claim 4 wherein said at least three sub-objects each comprise disks.

9. An X-ray diagnostic apparatus as claimed in claim 2 wherein said at least two sub-objects have respectively different radiation absorption characteristics.

10. An X-ray diagnostic apparatus as claimed in claim 1 wherein said reference object comprises a plurality of regions with at least two of said regions having different radiation-absorbing characteristics.

* * * * *